United States Patent [19]

Houlihan

[11] B 3,985,799

[45] Oct. 12, 1976

[54] 2-FLUORO-6-TRIFLUOROMETHYLBENZOIC ACID

[75] Inventor: William J. Houlihan, Mountain Lakes, N.J.

[73] Assignee: Sandoz, Inc., E. Hanover, N.J.

[22] Filed: Aug. 20, 1973

[21] Appl. No.: 390,031

[44] Published under the second Trial Voluntary Protest Program on January 13, 1976 as document No. B 390,031.

Related U.S. Application Data

[63] Continuation-in-part of Ser. No. 107,455, Jan. 18, 1971, abandoned, which is a continuation-in-part of Ser. No. 95,405, Dec. 4, 1970, abandoned, which is a continuation-in-part of Ser. No. 12,864, Feb. 19, 1970, abandoned, which is a continuation-in-part of Ser. No. 884,011, Dec. 10, 1969, abandoned.

[52] U.S. Cl. .................... 260/515 A; 260/521 H; 260/599; 260/612 D; 260/650 R; 260/650 F; 260/651 R; 260/651 F; 71/84
[51] Int. Cl.² .......................................... C07C 63/12
[58] Field of Search ............................. 260/515 A

[56] References Cited

UNITED STATES PATENTS

| | | | |
|---|---|---|---|
| 3,592,842 | 7/1971 | Houlihan | 260/515 |
| 3,624,087 | 11/1971 | Beck | 260/515 |

FOREIGN PATENTS OR APPLICATIONS

| | | | |
|---|---|---|---|
| 1,112,509 | 8/1961 | Germany | 260/515 |
| 817,173 | 7/1959 | United Kingdom | 260/515 |

OTHER PUBLICATIONS

Houlihan I, Chem. Abstracts, vol. 72 (1970), p. 401.
Houlihan II, Chem. Abstracts, vol. 75 (1971), p. 422.

*Primary Examiner*—James A. Patten
*Attorney, Agent, or Firm*—Gerald D. Sharkin; Robert S. Honor; Thomas O. McGovern

[57] ABSTRACT

2,6-halo and trifluoromethyl-substituted-benzoic acids, e.g., 2,3,4,6-tetrafluorobenzoic acid or 2-chloro-6-trifluoromethylbenzoic acid, are prepared from substituted 2,4-halo and trifluoromethyl-substituted benzene compounds and are useful as plant growth regulators.

1 Claim, No Drawings

2-FLUORO-6-TRIFLUOROMETHYLBENZOIC ACID

This application is a continuation-in-part of U.S. patent application Ser. No. 107,455, filed Jan. 18, 1971, which in turn is a continuation-in-part of U.S. patent application Ser. No. 95,405, filed Dec. 4, 1970, which is a continuation-in-part of U.S. patent application Ser. No. 12,864, filed Feb. 19, 1970, which in turn is a continuation-in-part of U.S. patent application Ser. No. 884,011, filed Dec. 10, 1969 all now abandoned.

This application relates to novel 2,6-halo and trifluoromethyl-substituted-benzoic acids, their preparation, and their use as plant growth regulators.

The compounds of this invention may be represented by the formula:

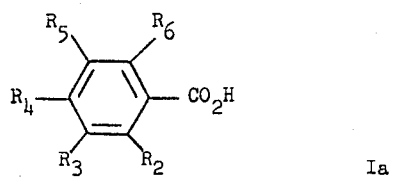

wherein
  $R_2$ represents halo having an atomic weight of about 19 to 36 or trifluoromethyl;
  $R_3$ is hydrogen, alkyl of 1 to 4 carbon atoms, allyloxy or halo having an atomic weight of about 19 to 36;
  $R_4$ is hydrogen or halo having an atomic weight of about 19 to 36;
  $R_5$ is hydrogen; and
  $R_6$ represents halo having an atomic weight of about 19 to 36, or trifluoromethyl with the provisos that
   a. at least one of $R_2$ and $R_6$ is halo;
   b. at least one of $R_2$ and $R_6$ is other than chlorine except when $R_3$ is allyloxy,
   c. $R_3$ is hydrogen only when at least one of $R_2$ and $R_6$ is $-CF_3$, and
   d. at least two of $R_2$, $R_3$ and $R_6$ are different when $R_4$ is hydrogen, or an agriculturally acceptable salt thereof.

The present invention also provides a plant growth regulator composition comprising a compound of formula (I):

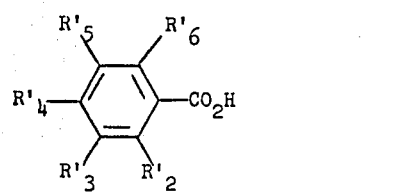

wherein
  $R_2'$ and $R_6'$ are each halo having an atomic weight of about 19 to 36 or trifluoromethyl,
  $R_3'$ is hydrogen, alkyl of 1 to 4 carbon atoms, alkoxy of 1 to 4 carbon atoms, allyloxy, halo having an atomic weight of about 19 to 36 or trifluoromethyl,
  $R_4'$ is hydrogen or halo having an atomic weight of about 19 to 36, and
  $R_5'$ is hydrogen, halo having an atomic weight of about 19 to 36 or trifluoromethyl, with the provisos that
   a'. at least one of $R_2'$ and $R_6'$ is halo,
   b'. there are no trifluoromethyl groups on adjacent carbon atoms of the aromatic nucleus,
   c'. at least one of $R_2'$, $R_3'$, $R_5'$ and $R_6'$ is other than halo,
   d'. when $R_3'$ is methyl, chlorine or trifluoromethyl and $R_4'$ and $R_5'$ are hydrogen, at least one of $R_2'$ and $R_6'$ is other than chlorine,
   e'. when $R_6'$ is trifluoromethyl and $R_4'$ and $R_5'$ are hydrogen, at least one of $R_2'$ and $R_3'$ is other than chlorine, and
   f'. when $R_3'$, $R_4'$ and $R_5'$ are each hydrogen at least one $R_2'$ and $R_6'$ is other than chlorine, or an agriculturally acceptable salt thereof as active agent, in association with an agricultural carrier or diluent.

The present invention further provides a process for the production of a compound of formula (Ia), comprising reacting a compound of formula (IIa):

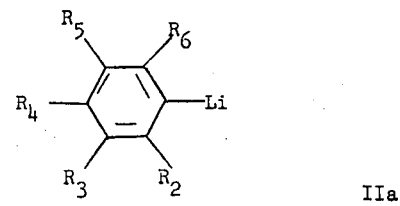

wherein $R_2$, $R_3$, $R_4$, $R_5$ and $R_6$ and the provisos thereto are as defined above, with carbon dioxide in a solvent inert under the reaction conditions, and when required converting the resulting compound into an agriculturally acceptable salt thereof. The reaction is carried out at a temperature of between $-50°$ and $-10°C.$, preferably between $-50°$ and $-25°C$. The carbon dioxide may be employed in gaseous or solid form. The solvent may be, for example, a lower hydrocarbon such as benzene, pentane, hexane or heptane, or an ether such as diethyl ether, dibutyl ether or tetrahydrofuran. The reaction is preferably effected in the absence of oxygen, e.g., by effecting the reaction in an inert atmosphere, for example, an atmosphere of nitrogen, helium or argon. The compound of formula (Ia) may be isolated by conventional techniques, e.g., by recrystallization or chromatography.

The compounds of formula (IIa), employed as starting materials in the production of compounds of formula (Ia), are novel and may be produced by reacting a compound of formula (IIIa):

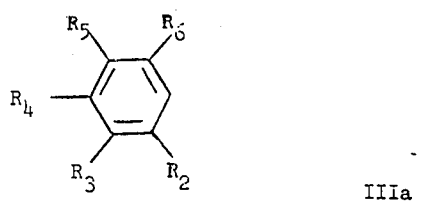

wherein $R_2$, $R_3$, $R_4$, $R_5$ and $R_6$ and the provisos thereto are as defined above, with a compound of formula (IV):

R—Li      IV wherein
  R is a straight chain alkyl of 1 to 6 carbon atoms, e.g., methyl, ethyl, n-propyl or n-butyl; in a solvent which is inert under the reaction conditions and in the absence of oxygen at a temperature of −60° to −30°C.

The preferred compound of formula (IV) is butyl lithium. The solvent may be, for example, a lower hydrocarbon such as benzene, pentane, hexane or heptane, or an ether such as diethyl ether, dibutyl ether or tetrahydrofuran. The absence of oxygen may be achieved by effecting the reaction in an inert atmosphere, for example, an atmosphere of nitrogen, helium or argon. The reaction is preferably effected at a temperature of between −50° and −40°C.

The process for the production of compounds of formula (IIa) may result in a mixture of isomers, depending on the number, position and type of substituents on the aromatic nucleus of the compound of formula (IIIa). In the case of a mixture of isomers, these need not be isolated or separated one from another but may be used as such in the production of a compound of formula (Ia) by the process hereinbefore described.

The compounds of formula (IV) and many of the compounds of formula (IIIa) are either known and may be prepared by processes disclosed in the literature. Insofar as compounds (IIIa) are not known, they may be prepared in a manner analogous to the disclosed processes using known starting materials.

Some of the compounds of formula (I) are known and may be prepared by methods disclosed in the literature. Insofar as they are not known, they may be prepared either in a manner analogous to the disclosed methods, or in a manner analogous to the method hereinbefore described for the production of compounds of formula (Ia).

The compounds of formulae (I) and (Ia) and agriculturally acceptable salts thereof, e.g., the sodium and potassium salts thereof, are useful as plant growth regulators. It is to be understood that the term "plant growth regulator" as used herein means that a growth function of a plant treated therewith, e.g., cell elongation, shoot growth, root growth, dormancy, flowering, leaf abscission, fruit thinning and fruit fall is affected. The term does not extend to a herbicidal property, i.e., to the destruction of the plant treated. Methods employed to determine the plant growth regulator activity of the compounds of formulae (I) and (Ia) are as follows:

TEST METHOD A

Cell elongation

Plant: *Cucumis sativus* L.

Cucumber seeds are pregerminated at approximately 25°C. in Molisch dishes on moist filter paper in the dark. After four days seedlings whose hypocotyls are 6 to 7 cm. in length are selected. Hypocotyl segments are prepared by cutting the hypocotyls with a razor blade 3.0 cm. below the base of the cotyledons. Cotyledons are removed or left attached to the segments. Sets of 10 hypocotyl segments are incubated at 25°C. in the dark in covered dishes each containing 50 cc. of test solution.

The test solutions employed (Knop nutrient solutions diluted with water to 1/5) contain the test compounds in concentrations of 100, 10, 1 and 0.1 p.p.m. After 48 hours the length of the hypocotyls are measured and compared with control plants. All manipulations except the length measurements are carried out in red light in a dark room.

TEST METHOD B

Germination rate, shoot and root growth (cell elongation and cell division)

Plant: *Avena sativa* L.

Oat seeds are placed on a wire gauze having a mesh of appropriate size. The gauze touches the surface of a Knop nutrient solution in a beaker, the solution containing the test compounds in concentrations of 10, 1 and 0.1 ppm. Fifteen seeds are used per beaker. The germination rate is determined and the longitudinal growth of the shoots as well as of the roots and other growth effects (e.g. curvatures) are evaluated visually in comparison with control plants.

TEST METHOD C

Leaf abscission (Defoliation)

Plant: *Phaseolus vulgaris* L.

Explants are prepared from 3 week old bean plants (cultivation carried out in a mixture of peat medium substrate and sand). The explants consist of the petiole stumps of the primary leaves and a part of the epicotyl attached. The compounds to be tested are mixed in concentrations of 1000, 100 and 10 ppm with 0.1% warm agar. Five microliters of the still warm mixture are applied on the cut surface of the petioles with a springe. The number of petioles that abscise after application of constant pressure is recorded daily and compared with the number of petioles abscised of the control plants (pure 0.1% agar).

Following are results using the above test procedures obtained with representative compounds embraced by this invention at the part per million dosages (p.p.m.) shown:

1. 2,6-difluoro-m-toluic acid
   a. Moderate leaf abscission at 1000 p.p.m.
2. 2,3-dichloro-6-fluorobenzoic acid
   a. Moderate germination checking at 10 p.p.m.
   b. Moderate shoot growth checking at 10 p.p.m.
   c. Strong root growth checking at 10 p.p.m.
3. 2-chloro-6-fluoro-m-toluic acid
   a. Moderate cell elongation checking with cotyledons at 100 p.p.m.
   b. Moderate cell elongation promotion without cotyledons at 100 p.p.m.
   c. Moderate shoot growth checking at 10, 1 and 0.1 p.p.m.
   d. Strong root growth checking at 10 and 1 p.p.m.
   e. Moderate root growth checking at 0.1 p.p.m.
   f. Moderate leaf abscission at 1000 p.p.m.
4. 3-allyloxy-2,6-dichlorobenzoic acid
   a. Moderate cell elongation checking with cotyledons at 100 p.p.m.
5. 2-chloro-6-trifluoromethylbenzoic acid
   a. Moderate cell elongation promotion with cotyledons at 0.1 p.p.m.
   b. Moderate root growth checking at 10 p.p.m.
   c. Moderate leaf abscission at 1000 p.p.m.
6. 2,3,4,6-tetrafluorobenzoic acid
   a. Moderate root growth checking at 10 p.p.m.
7. 2,6-dichloro-3-methoxybenzoic acid
   a. Moderate root growth checking at 10 p.p.m.
   b. Moderate leaf abscission at 1000 p.p.m.
8. 2,6-dichloro-m-toluic acid
   a. Moderate cell elongation promotion with cotyledons at 0.1 p.p.m.

b. Moderate shoot growth checking at 10 p.p.m.
c. Strong root growth cehcking at 10 and 1 p.p.m.
d. Moderate leaf abscission at 1000 p.p.m.

The compounds of formulae (I) and (Ia) and the agriculturally acceptable salts thereof may be employed as pre-emergence or post-emergence plant growth regulators. To this end they are employed in association with an agriculturally acceptable carrier or diluent. The compounds may be applied to a desired locus by spraying, watering or dusting using conventional applicator equipment. The preferred method of application is spraying the compounds either in suspension or solution.

Liquid formulations containing the compounds of formula (I) which are used in direct spraying may be prepared with water, petroleum fractions, liquid aliphatic or aromatic alcohols, esters, glycols or ketones and the like. These liquid formulations may be solution, dispersions, emulsions, or wettable powder dispersion and may contain surface active agents, e.g., wetting agents, dispersing agents, emulsifying agents and the like, in sufficient amounts to impart the desired characteristics to the formulation.

Aqueous formulations may be made by adding water to a concentrated emulsion, paste or wettable spray powder containing the active ingredient using a wetting, emulsifying or dispersing agent which may be either anionic, cationic, non-ionic or mixtures thereof. Dusts may be prepared by mixing or grinding the active ingredient with a solid carrier material such as talc, diatomaceous earth, kaolin, bentonite, calcium carbonate, boric acid, calcium phosphate, wood, flour, cork, dust, carbon and the like. Scatterable granules may be obtained, for example, by using ammonium sulfate as carrier material. Alternatively, carrier materials may be impregnated with solutions of the active ingredient in liquid solvents. Powder preparations or pastes which can be suspended in water and used as sprays may be obtained by adding wetting agents and protective colloids to the active agent. The application forms may also contain additional ingredients which improve dispersion, adhesion, resistance to rain, and penetrative power such as fatty acids, resins, wetting agents, emulsifying agents, glue and the like.

The plant growth regulator effective dosage of the compounds of formula (I) and (Ia) and their agriculturally acceptable salts will naturally vary depending upon such factors as the desired effect, the age of the plants, the culture medium, ambient temperature, humidity and light. The compounds will generally be applied at a dosage of 0.05 to 10 pounds per acre to produce a satisfactory plant growth regulator effect. An appropriate non-selective dosage is 0.5 to 1.5 pounds per acre for pland growth regulation whereas a dosage suitable for selective agrochemical action is 0.05 to 0.5 pound per acre. Formulations for use in application forms may contain between 10 and 95% by weight of the compounds, preferably between 50 and 85% by weight. Application forms will generally contain between 0.0001 and 1% by weight of the compounds.

The preferred compounds of formula (I) may be represented by the following formula:

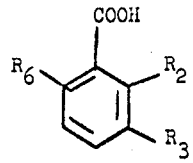

where
$R_2$ is fluorine or chlorine
$R_3$ is hydrogen, alkyl of 1 to 4 carbon atoms, or allyloxy and
$R_6$ is fluorine, chlorine or trifluoromethyl with the provisos that
a. at least one of $R_2$ and $R_6$ is halo
b. at least one of $R_2$ and $R_6$ is other than chlorine except when $R_3$ is allyloxy and
c. $R_3$ is hydrogen only when at least one of $R_2$ and $R_6$ is $-CF_3$, or an agriculturally acceptable salt thereof.

The especially preferred compounds are 2-chloro-6-trifluoromethyl-benzoic acid, 2,3,4,6-tetrafluorobenzoic acid, 2-chloro-6-fluoro-m-toluic acid, 6-chloro-2-fluoro-m-toluic acid, 2,3-dichloro-6-fluorobenzoic acid and 3-allyloxy-2,6-dichlorobenzoic acid, and particularly 2-chloro-6-trifluoromethylbenzoic acid, 2,3,4,6-tetrafluorobenzoic acid, and 2,3-dichloro-6-fluorobenzoic acid.

The compounds of formula (Ia) in which $R_6$ is trifluoromethyl, $R_3$, $R_4$ and $R_5$ are hydrogen and $R_2$ is chlorine or fluorine are also useful as intermediates in the preparation of 2-halo-6-trifluoromethyl-phenylacetaldehydes which are used in the preparation of compounds having hypotensive activity as disclosed in Netherland application 7,000,045 filed Jan. 5, 1970 and published July 13, 1969. The 2-halo-6-trifluoromethyl-benzoic acids are converted to the corresponding 2-halo-6-trifluoromethyl-phenylacetaldehyde by standard techniques, e.g., aminating the acid, converting the amide to the 2-halo-6-trifluoromethylbenzylnitrile; reducing the nitrile to the corresponding benzaldehyde and reducing the benzaldehyde to the corresponding benzyl alcohol; forming the benzyl bromide and then the 2-halo-6-trifluoromethyl-phenylacetonitrile; and thereafter reducing the phenylacetonitrile to the 2-halo-6-trifluoromethyl-phenylacetaldehyde. The 2-halo-6-trifluoromethyl-phenylacetaldehydes are converted to the hypotensive agents, 2-(2-halo-6-trifluoromethyl-phenyl)-5,6-dihydroimidazo[2,1-b]-thiazole hydrobromide, in accordance with the procedure disclosed in the aforementioned Netherland patent application, i.e. by brominating the acetaldehyde; treating the α-bromo-2-halo -6-trifluoromethylphenylacetaldehyde thus formed with ethylene thiourea and thereafter dehydrating the resulting intermediate to form the pharmaceutically active product.

EXAMPLE 1

2,6-difluoro-m-toluic acid

Into a flask equipped with stirrer, dropping funnel, carbon dioxide condenser and gas inlet tube are charged 100 g. (0.78 mole) of 2,4-difluoro-toluene and 500 ml. of dry tetrahydrofuran. The system is flushed with dry nitrogen and cooled (carbon dioxide-acetone bath) to an internal temperature of −50°C. A 585 ml. solution of 15% n-butyllithium (0.935 mole n-butyllithium) in hexane is added dropwise into a flask. The resulting dark red-purple solution is maintained at −50°C. for about one hour, and then poured onto a slurry of about 1000 g. of powdered carbon dioxide and about 100 ml. of diethyl ether. After standing for about 20 hours at room temperature the residue is treated with 250 ml. of 2N sodium hydroxide. The caustic layer is washed with toluene, acidified with concentrated HCl, and the white precipitate which forms is recrystallized from hot chloroform to give 2,6-difluoro-m-toluic acid; m.p. 139°–140°C.

Following the above procedure, but using an equivalent amount of 2-chloro-4-fluorotoluene; 4-chloro-2-fluorotoluene; 3,4-dichloro-1-fluoro-benzene; 1,3,4,5-tetrafluorobenzene; 2,4-dichloroanisole; 3-fluoro-1-trifluoromethylbenzene, 2,4-dichloro-1-allyloxybenzene or 3-chloro-1-trifluoromethylbenzene in place of the 2,4-difluorotoluene used therein there is obtained 2-chloro-6-fluoro-m-toluic acid (m.p. 116°–117°C); 2-fluoro-6-chloro-m-toluic acid (mp. 113°–134°); 2,3-dichloro-6-fluorobenzoic acid (mp. 133°–134°C); 2,3,4,6-tetrafluorobenzoic acid (mp. 143°–145°C.); 2,6-dichloro-3-methoxybenzoic acid (mp. 145°–147°C.); 2-fluoro-6-trifluoro methylbenzoic acid (mp. 84°–85°C); 3-allyloxy-2,6-dichlorobenzoic acid (mp. 143°–144°C) or 2-chloro-6-trifluoromethylbenzoic acid (mp. 122°–124°C).

What is claimed is:
1. The compound which is 2-fluoro-6-trifluoromethyl benzoic acid.

* * * * *